United States Patent [19]
Erickson

[11] 4,370,979
[45] Feb. 1, 1983

[54] SUSPENSORY URINAL SHEATH EXPANDER

[76] Inventor: Dale L. Erickson, Box 283, Frederic, Wis. 54837

[21] Appl. No.: 257,429

[22] Filed: Apr. 21, 1981

[51] Int. Cl.³ .............................................. A61B 17/00
[52] U.S. Cl. ................................ 128/303 A; 128/20; 128/294; 128/295
[58] Field of Search ................... 433/3; 4/144.1–144.4; 248/99, 100, 101, 95; 128/294, 295, 303 A, 283, 136, 79, 20, 127

[56] References Cited

U.S. PATENT DOCUMENTS

| | | | |
|---|---|---|---|
| 2,447,474 | 8/1948 | Hammond | 128/303 A |
| 2,840,081 | 6/1958 | Moose | 128/303 A |

FOREIGN PATENT DOCUMENTS 135438  6/1933  Austria ................................ 128/127

*Primary Examiner*—Richard J. Apley
*Assistant Examiner*—J. L. Kruter
*Attorney, Agent, or Firm*—Harvey B. Jacobson

[57] ABSTRACT

A pair of stationary divergent arm portions are provided including base and free ends. The free ends are spaced apart and the base ends are stationarily joined together. Guide structure is stationarily supported relative to the base ends of the arm portions and a movable jaw is guidingly supported from the guide structure for movement toward and away from the free ends of the arm portions along a path disposed generally normal to a path extending between the arm portion free ends. The free ends of the arm portions include parallel elongated jaw elements projecting therefrom in directions disposed generally normal to the aforementioned paths and the movable jaw includes an elongated jaw element generally paralleling the aforementioned jaw elements. The three jaw elements may be inserted into the inlet end portion of a urinal sheath and the movable jaw may be shifted away from the arm portion free ends whereby the inlet end of the sheath will be spread for free unobstructed insertion of a penis thereinto.

6 Claims, 4 Drawing Figures

U.S. Patent  Feb. 1, 1983  4,370,979 ated in FIGS. 2 and 3 of the drawings with the
SUSPENSORY URINAL SHEATH EXPANDER

BACKGROUND OF THE INVENTION

Many males who must use a suspensory type urinal are physically disabled in the areas of their arms or hands and have difficulty in installing a suspensory type urinal sheath. Accordingly, a need exists for means by which a male may properly apply the sheath of a suspensory type urinal through the utilization of only one hand.

Examples of previously known structures, including some of the general structural and operational features of the instant invention, are disclosed in U.S. Pat. Nos. 3,749,088, 3,965,890, 3,998,217, 4,010,741 and 4,155,355. However, these previously known devices are not specifically designed for expanding and supporting the sheath of a suspensory type male urinal for ready application of the urinal sheath to a penis.

BRIEF DESCRIPTION OF THE INVENTION

The sheath expander of the present invention includes a pair of elongated parallel stationary jaw elements for insertion into one side portion of a suspensory type urinal sheath and a third elongated movable jaw element generally paralleling the first mentioned jaw elements is supported for lateral movement toward and away from a path extending between the first mentioned jaw elements. in this manner, the three jaw elements may be inserted into the inlet end of the sheath of a suspensory type male urinal and the movable jaw element may be shifted away from the stationary jaw elements in order to expand the sheath and to support the inlet end portions thereof in an unobstructed expanded manner for ready free insertion of a penis into the sheath.

The sheath expander is constructed in a manner whereby the sheath, once having been applied to an associated penis, may be laterally displaced outwardly from between the stationary jaw elements of the expander.

The main object of this invention is to provide a male suspension urinal sheath expander which may be utilized by physically disabled persons for proper application of the sheath of a male suspensory type urinal to a penis through the utilization of only one hand.

Another object of this invention is to provide a sheath expander which may be utilized in conjunction with sheaths of different sizes.

Another object of this invention is to provide a suspension urinal sheath expander which may be utilized by blind physically disabled persons.

A final object of this invention to be specifically enumerated herein is to provide a suspensory type urinal sheath expander in accordance with the preceding objects and which will conform to conventional forms of manufacture, be of simple construction and easy to use, so as to provide a device that will be economically feasible, long lasting and relatively trouble-free in operation.

These together with other objects and advantages which will become subsequently apparent reside in the details of construction and operation as more fully hereinafter described and claimed, reference being had to the accompanying drawings forming a part hereof, wherein like numerals refer to like parts throughout.

DETAILED DESCRIPTION OF THE INVENTION

Figure 1:
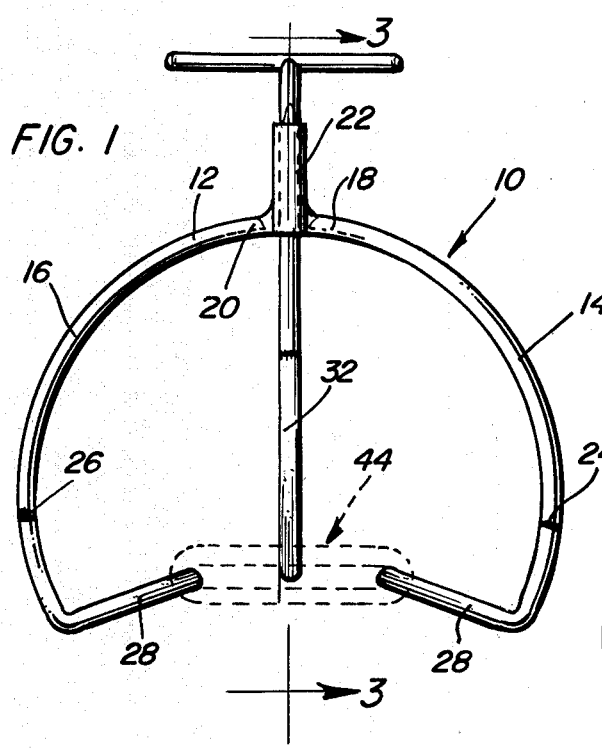
FIG. 1 is a front elevational view of the expander with the relatively movable components thereof in positions for initial application to a urinal sheath.

Referring now more specifically to the drawings, the numeral 10 generally designates the sheath expander of the instant invention. The expander 10 includes a frame 12 comprising a pair of stationary arcuate arm portions 14 and 16 which are generally quarter circular in configuration and coextensive. The arm portions include adjacent ends 18 and 20 which are integrally formed and from which a guide sleeve 22 is supported. The arm portions 14 and 16 include remote spaced apart ends 24 and 26 each including an L-shaped jaw member supported therefrom and the jaw members include terminal end parallel jaw elements 30 which are equally spaced apart on opposite sides of the longitudinal center line of the guide sleeve 22.

A support rod 32 is slidingly received through the guide sleeve 22 and includes a right angled jaw element 34 on its end adjacent the jaw members 30 and which parallels the latter. The jaw element 34, when the rod 32 is displaced toward the jaw elements 30, is positionable centrally intermediate the jaw elements 30 along a line extending between the latter. The end of the support rod 32 remote from the jaw element 34 carried a cross head 36 and the rod 32 includes an outwardly projecting nib 38 closely spaced from the cross head 35 and which is engageable with the opposing end of the guide sleeve 22.

Figure 2:
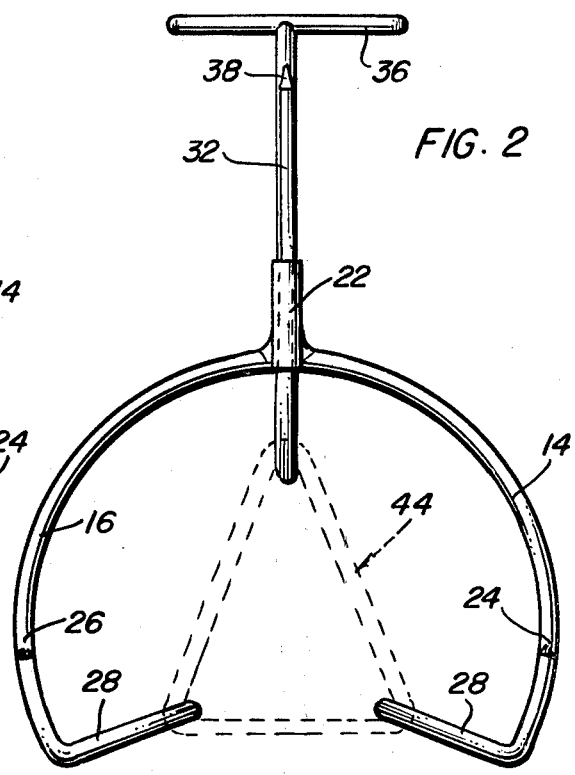
FIG. 2 is an elevational view, similar to FIG. 1, but with the relatively movable components in their positions which are assumed when the associated sheath is expanded.
Figure 3:
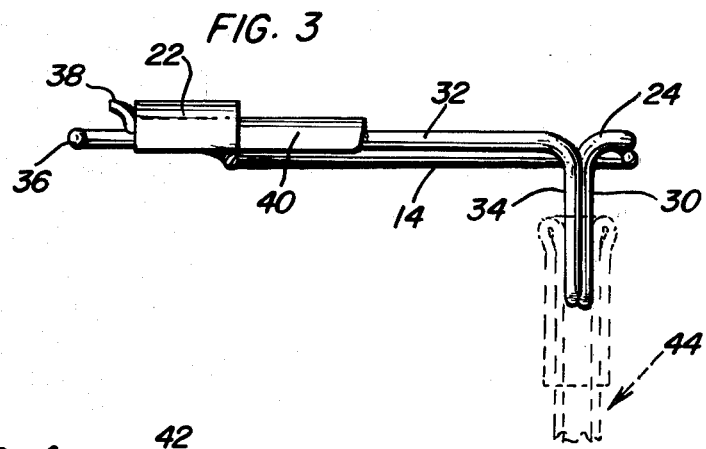
FIG. 3 is a fragmentary, vertical sectional view taken substantially upon the plane indicated by the section line 3—3 of FIG. 1.

In addition, the rod 32 includes a sleeve 40 stationarily mounted thereon and the sleeve 40 is loosely receivable through the guide sleeve 22, but includes a beveled end 42 opposing the jaw element 34 and which is engageable with the end of the sleeve 22 remote from the jaw element 34 when the rod 32 is the position thereof illustrated in FIGS. 2 and 3 of the drawings with the jaw element 34 retracted away from a plane containing the jaw elements 30.

Figure 4:
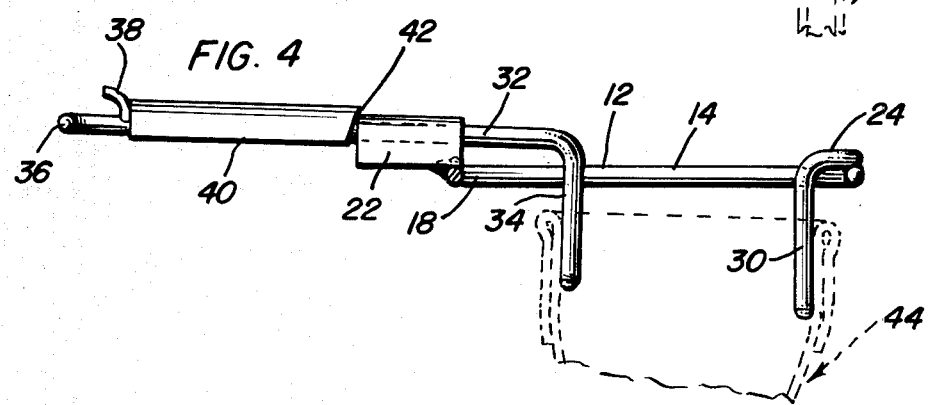
FIG. 4 is a sectional view similar to FIG. 3 but illustrating the relatively movable components of the expander in the positions thereof when being utilized to expand an associated urinal sheath.

The reference numeral 44 generally designates the inlet end of the sheath of a suspensory-type male urinal and the rod 32 is first positioned in the manner illustrated in FIGS. 1 and 3 of the drawings with the inlet end of the sheath 44 engaged over the jaw elements 30 and 34. Thereafter, the rod 32 is displaced upwardly from the position thereof illustrated in FIG. 1 of the drawings relative to the frame 12 to the position thereof illustrated in FIG. 2. In this manner, the inlet end of the sheath 44 is stretched and defines an unobstructed large cross-sectional opening into which the user's penis may be readily inserted. When the rod 32 is displaced from the position thereof illustrated in FIG. 1 to the position thereof illustrated in FIG. 2 against the resiliency of the sheath 44 with which the jaw elements 30 and 34 are engaged, the end of the sleeve 40 adjacent the jaw element 34 is laterally displaced so as to engage the beveled end 42 of the sleeve 44 over the opposing end of the sleeve 22. In this manner, the jaw elements 30 and 34 will be retained in the positions thereof illustrated in FIGS. 2 and 4 of the drawings. Of course, after the user's penis has been inserted into the enlarged inlet end of the sheath 44, the rod 32 is oppositely laterally displaced in order to disengage the beveled end 42 from the adjacent end of the sleeve 22 and thereby allow the rod 32 to shift, at least slightly, from the position thereof illustrated in FIG. 2 toward the position thereof illustrated in FIG. 1. As the jaw elements 30 and 34 engage the outer surfaces of the penis over which the sheath 44 is disposed, the jaw elements 30 and 34 may be withdrawn from the sheath 44. Thereafter, the sheath may be laterally displaced from the expander 10 between the jaw elements 30.

It is pointed out that the frame 12 could be inverted V-shaped in configuration, that the jaw elements could be arcuate in cross section, that the support rod 32 could be spring biased to the position thereof illustrated in FIG. 2 and that the jaw elements could be slightly divergent toward their free ends. Also, the arm portions are disposed outside a triangular area having the jaw elements at its corner portions.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. A urinal sheath support and expander including first stationary jaw means for insertion into the inlet end portion of a urinal sheath in close opposition to the internal surfaces of said inlet end portion at one side thereof, second movable jaw means guidingly supported from said stationary jaw means and for insertion into said inlet end portion in close opposition to the internal surfaces of said sheath at the other side thereof, said movable jaw means being supported from said stationary jaw means for shifting away from said stationary jaw means, said stationary and movable jaw means, when shifted away from each other, being operable to spread to inlet end portion of said sheath for free unobstructed insertion of a penis thereinto, said stationary jaw means including a pair of divergent arm portions including base and free ends, said free ends being spaced apart, means joining said base ends, guide structure stationarily supported relative to said base ends, a support rod shiftably supported from said guide structure and including a free end advanceable to a position disposed in a path extending between the free ends of said divergent arm portions, said free ends including elongated generally parallel jaw elements disposed generally normal to said arm portions and rod, said rod being displaceable away from said free ends of said arm portions to thereby displace the jaw element carried by said rod laterally away from a plane containing the jaw elements supported from said free ends of said arm portions, said divergent arm portions being generally quarter circular in shape and the base ends thereof being coextensive, said guide structure being supported from the base ends of said arm portions, said guide structure comprising a guide sleeve through which said rod is longitudinally slidably received, said free ends of said divergent arm portions being spaced substantially equally on opposite sides of the longitudinal center line of said sleeve.

2. The combination of claim 1 wherein said guide structure and rod include coacting structure operable to releasably retain said rod in a shifted position with the jaw element of said rod displaced away from the plane containing the jaw elements supported from the free ends of said divergent arm portions.

3. A support and expander assembly for a urinal sheath, said assembly including a pair of laterally spaced apart generally parallel elongated and relatively stationary jaw elements, a third jaw element, means mounting said third jaw element from said stationary jaw elements for movement relative thereto between a first position in which said third jaw element generally parallels said pair of jaw elements, is disposed on a straight line extending between said pair of jaw elements and is substantially equally spaced between said pair of jaw elements and a second position generally paralleling said pair of jaw elements and displaced laterally of a plane containing said pair of jaw elements and with said movement occurring independent of relative shifting of said stationary jaw elements, and means operatively connected to said third jaw element for shifting said third jaw element between said first and second positions thereof.

4. A urinal sheath support and expander including first stationary jaw means for insertion into the inlet end portion of a urinal sheath in close opposition to the internal surfaces of said inlet end portion at one side thereof, second jaw means guidingly supported from said stationary jaw means and for insertion into said inlet end portion in close opposition to the internal surfaces of said sheath at the other side thereof, said second jaw means being supported from said stationary jaw means for shifting away from said stationary jaw means, said stationary and second jaw means, when shifted away from each other, being operable to spread to inlet end portion of said sheath for free unobstructed insertion of a penis thereinto, said stationary jaw means including a pair of divergent arm portions including base and free ends, said free ends being spaced apart, means joining said base ends, guide structure stationarily supported relative to said base ends, a support rod shiftably supported from said guide structure and including a free end advanceable to a position disposed in a path extending between the free ends of said divergent arm portions, said free ends including elongated generally parallel jaw elements disposed generally normal to said arm portions and rod, said rod being displaceable away from said free ends of said arm portions to thereby displace the jaw element carried by said rod laterally away from a plane containing the jaw elements supported from said free ends of said arm portions, said guide structure comprising a guide sleeve through which said rod is longitudinally slidably received, said free ends of said divergent arm portions being spaced substantially equally on opposite sides of the longitudinal center line of said sleeve.

5. A support and expander for a urinal sheath, said support and expander including a pair of elongated and generally parallel laterally spaced apart jaw means including corresponding base and free ends, connecting structure extending between and relatively stationarily mounting said pair of jaw means, third elongated jaw means generally paralleling and laterally spaced equally between said pair of jaw means along a straight line extending therebetween, said third jaw means including base and free ends corresponding to the first mentioned base and free ends, an elongated support member from one end portion of which said base end of said third elongated jaw means is supported with said support member disposed generally normal to a plane containing said pair of jaw means, said connecting structure including guide means mounting said support member for longitudinal reciprocation relative to said connecting structure and for movement of said third jaw means between a first position disposed in said plane and a second position laterally spaced outwardly of one side of said plane, said guide means being spaced outwardly of said one side of said plane and said connecting structure including a pair of divergent arms having base and free ends from which said guide means and pair of jaw means, respectively, are supported, the spacing between said pair of jaw means being such that the elastic inlet end of a urinal sheath may be snugly engaged over the free ends of said pair of jaw means with the free end of said third jaw means projecting into said inlet end between said pair of jaw means when said third jaw means is disposed in said first position.

6. The support and expander of claim 5 wherein said divergent arm portions are generally quarter circular in shape and the base ends thereof are generally coextensive.

* * * * *